United States Patent [19]

DiGiulio

[11] 4,017,641
[45] Apr. 12, 1977

[54] SKIN MOISTURIZING COMPOSITIONS CONTAINING 2-PYRROLIDINONE

[75] Inventor: David Neil DiGiulio, Springfield Township, Hamilton County, Ohio

[73] Assignee: The Procter & Gamble Company, Cincinnati, Ohio

[22] Filed: Jan. 31, 1975

[21] Appl. No.: 545,938

[52] U.S. Cl. ............................. 424/365; 252/316; 424/73; 424/81

[51] Int. Cl.² ......................................... A61K 7/48

[58] Field of Search ............... 424/73, 81, 365; 252/316

[56] References Cited

UNITED STATES PATENTS

| | | | |
|---|---|---|---|
| 2,757,125 | 7/1956 | Mudrak | 424/274 X |
| 3,235,457 | 2/1966 | Laden | 424/73 X |
| 3,836,665 | 9/1974 | Eberhardt et al. | 424/274 |

FOREIGN PATENTS OR APPLICATIONS 2,416,556  5/1974  Germany

OTHER PUBLICATIONS

Chemical Abstracts, vol. 73, 102083(d), (1970).

*Primary Examiner*—Albert T. Meyers
*Assistant Examiner*—Vera C. Clarke
*Attorney, Agent, or Firm*—Ronald L. Hemingway; George W. Allen

[57] ABSTRACT

Skin conditioning compositions of the oil-in-water emulsion type containing 2-pyrrolidinone, wherein a substantial amount of the 2-pyrrolidinone is present in the oil phase.

6 Claims, No Drawings

SKIN MOISTURIZING COMPOSITIONS CONTAINING 2-PYRROLIDINONE

DESCRIPTION OF THE INVENTION

The present invention provides compositions which improve the condition of skin through moisturization and flexibilization. The application of oils or of oil-in-water emulsions to the skin so as to form a barrier which reduces the escape of moisture from the skin is known to the art. Also, the incorporation into said oils or emulsions of humectant-type materials to exert a positive moisturizing effect on the skin is known. Increased moisture content is believed to be either directly or indirectly responsible for increasing the flexibility of the skin.

In accordance with the present invention the chemical, 2-pyrrolidinone, which heretofore has not been successfully used for this purpose, is used as a skin moisturizing and flexibilizing ingredient in oil-in-water emulsions. According to the present invention it has been found that in order for 2-pyrrolidinone to be effective it must be formulated into such emulsions with a proper view to the selection of the oil components, the emulsifiers, and the method by which the emulsion is prepared so as to ensure that a substantial portion of the 2-pyrrolidinone remains in the oil phase of the emulsion.

The oil component of the present compositions can be any oil or mixture of oils, and/or wax or mixture of waxes which is physiologically acceptable for placement on the skin, and in which 2-pyrrolidinone is freely miscible when the oil component is in the liquid state. The term "freely miscible" as used herein shall mean that the 2-pyrrolidinone shall be completely miscible when mixed into the oil component to the extent of at least 50% by weight of 2-pyrrolidinone, based upon the total weight of oil component and 2-pyrrolidinone, at the minimum temperature at which the oil component exists as a liquid. In many instances the oil component will be solid at room temperature.

Examples of suitable oils and waxes which can make up the oil component of the compositions of the present invention are lanolin fatty acids (e.g., Amerlate WFA), isopropyl esters of lanolin fatty acids (e.g., Amerlate W) and hydroxylated lanolin (e.g., OH Lan). The foregoing three materials are available from Amerchol Co., a unit of CPC International. Other suitable oils and waxes include the aliphatic straight chain fatty acids and alcohols of from about 10 to about 20 carbon atoms, e.g., lauric acid, stearic acid, coconut fatty alcohol, cetyl alcohol and stearyl alcohol. Mixtures of the various oils and waxes can be used up to oil component of the compositions.

The oil component should comprise from about 1% to about 25% (preferably from about 5% to about 15%) by weight of the total composition.

An oil-miscible emulsifier (or mixture of emulsifiers) is an essential component of the present compositions and is used in an amount sufficient to form an oil-in-water emulsion between 2-pyrrolidinone, the water and the oil component of the present compositions. Generally the emulsifier comprises from about 0.05% to about 10% by weight of the composition. Generally the emulsifier should be miscible in the oil component to the extent of at least 25% by weight of the total weight of said emulsifier and said oil component at the minimum temperature at which said oil component is a liquid. Many oil-miscible emulsifiers are known to the art and are useful in the present invention. Generally, such emulsifiers are nonionic surfactants. One suitable type of nonionic surfactant is the fatty acid monoglyceride, wherein the fatty acid group contains from about 10 to about 20 carbon atoms, e.g., glycerol monostearate. Other suitable nonionic surfactants are the alkoxylated nonionics.

The alkoxylated nonionic surfactants may be broadly defined as compounds produced by the condensation of alkylene oxide groups (hydrophilic in nature) with an organic hydrophobic compound which may be aliphatic or alkyl-aromatic in nature. The length of the hydrophilic polyoxyalkylene radical which is condensed with any particular hydrophobic group can be readily adjusted to yield an oil-miscible compound having the desired degree of balance between hydrophilic and hydrophobic elements.

For example, a well-known class of nonionic synthetic detergents is made available on the market under the trade name of "Pluronic." These compounds are formed by condensing ethylene oxide with a relatively hydrophobic base formed by the condensation of propylene oxide with propylene glycol. The hydrophobic portion of the molecule which, of course, exhibits water insolubility, has a molecular weight of from about 1,500 to about 1,800. The condensation of ethylene oxide to this hydrophobic portion in an amount such that the polyoxyethylene content of the total condensation product is from about 5% to about 20% by weight produces oilmiscible emulsifiers which are highly suitable for use in the present compositions.

Other suitable alkoxylated nonionic surfactants include:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 2 to 20 moles of ethylene oxide per mole of alkyl phenyl. Th alkyl substituent in such compounds may be derived from polymerized propylene, diisobutylene, octane, or nonane, for example.

2. The condensation product of aliphatic alcohols having from 12 to 18 carbon atoms; in either straight chain or branched chain configuration, with from about 2 to about 20 moles of ethylene oxide or propylene oxide per mole of alcohol, e.g., a stearyl alcohol propylene oxide condensate having from 15 moles of propylene oxide per mole of stearyl alcohol.

2-pyrrolidinone, which is the active moisturizing ingredient of the present compositions, is a standard item of commerce, being used widely as a plasticizer and solvent. When formulated into oil-in-water emulsions according to the present invention, this compound exerts a substantial moisturizing and flexibilizing effect on the skin when the emulsion is spread upon the skin in the normal manner of skin lotion usage. The 2-pyrrolidinone is present in the compositions of the invention at levels of from about 1% to about 20% (preferably from about 5% to about 15%) by weight and is, as will be discussed hereinafter, incorporated into said compositions in a manner so as to ensure that there is a proper distribution of 2-pyrrolidinone between the oil phase and the water phase.

Water is an essential component of the compositions of the invention and is present at a level of from about 50% to about 95% by weight of the total composition.

In order to achieve the substantial skin moisturizing and flexibilizing benefits of 2-pyrrolidinone, the compositions of the present invention must be formulated according to the procedure which will ensure that a proper distribution of the 2-pyrrolidinone will be obtained between the water phase and oil phase of the emulsion. The procedure is as follows:

1. Liquify the oil component by bringing it to a temperature at which it is liquid.
2. Mix the emulsifier and from about 10% to about 95% (preferably from about 25% to about 75%) by weight of the total amount of 2-pyrrolidinone to be used in the composition into the liquified oil component.
3. Dissolve the balance of the 2-pyrrolidinone in the water component.
4. Mix the water component and oil component to form an emulsion.

Optionally, Step 3 in the above process can be performed after Step 4, i.e., the balance of the 2-pyrrolidinone can be added to the emulsion instead of adding it to the water component prior to forming the emulsion. The order in which the emulsifier and 2-pyrrolidinone are added to the oil component is not critical. Preferably, the water component is brought to the temperature of the liquified oil component before the two are mixed in Step 4 so that the two components will be at substantially the same temperature when they are mixed with each other.

In addition to the essential ingredients described above, the compositions of the present invention can contain additional materials which are commonly used in skin care preparations, e.g., viscosity modifiers such as the Carbopols (cross-linked carboxy polymethylene polymers), sorbitol and propylene glycol, preservatives such as the $C_1$ to $C_4$ alkyl esters of para hydroxy benzoic acid, opacifiers such as titanium dioxide, emulsion stabilizers such as triethanolamine, and dyes and fragrances. Although the points at which these optional ingredients are added to the compositions in the making process are not critical, it is preferable that such materials be incorporated into the composition by mixing them into the respective component (i.e., oil component or water component) in which they are soluble or readily dispersible, prior to forming the emulsion. If insoluble particulate materials such as opacifiers (e.g., $TiO_2$) are to be used in the compositons, it is preferable that they be added to the finished emulsion.

The present invention will be illustrated by the following example.

The following composition is prepared:

| | The following composition is prepared: | |
|---|---|---|
| 1. | Amerlate WFA[a] | 0.75 |
| 2. | Amerlate W[b] | 1.00 |
| 3. | Stearic acid | 1.00 |
| 4. | Cetyl alcohol | 1.75 |
| 5. | Stearyl alcohol | 0.75 |
| 6. | OH Lan[c] | 0.75 |
| 7. | Arlacel 165[d] | 0.75 |
| 8. | Arlamol E[e] | 1.25 |
| 9. | 2-pyrrolidinone | 8.00 |
| 10. | Distilled water | 74.55 |
| 11. | Carbopol 934[f] (15% solution in $H_2O$) | 3.25 |
| 12. | Propylene glycol | 2.50 |
| 13. | Sorbitol (70% solution in $H_2O$) | 2.50 |
| 14. | Triethanolamine | 0.65 |
| 15. | Methyl Paraben[g] | 0.20 |
| 16. | Propyl Paraben[h] | 0.10 |
| 17. | Titanium dioxide | 0.20 |
| 18. | Perfume | 0.05 |
| | | 100.00 |

[a]Mixture of lanolin fatty acids (Amerchol Unit of CPC International)
[b]Isopropyl ester of lanolin fatty acids (Amerchol Unit of CPC International)
[c]Hydroxylated lanolin (Amerchol Unit of CPC International)
[d]Glycerol monostearate (ICI United States, Inc.)
[e]Polyoxypropylene (15) stearyl ether (ICI United States, Inc.)
[f]Polymer of acrylic acid cross-linked with polyalkyl ether of sucrose, M.W. 1,000,000 (B. F. Goodrich Chemical Co.)
[g]Methyl ester of p-hydroxybenzoic acid (Washine Chemical Corp.)
[h]Propyl ester of hydroxybenzoic acid (Washine Chemical Corp.)

Ingredients 1–8 are mixed in a tank and heated to 82° C. and one-half of the 2-pyrrolidinone (i.e., 4%) is added. Mixing is continued for 30 minutes at 82° C. The mixture is homogeneous and liquid. Ingredients 10–14 are mixed in a second tank for 30 minutes at 82° C. The mixture is homogeneous and liquid. The contents of the two tanks are then mixed together. After about 5 minutes of mixing, ingredients 15–17 are added to the mixture and agitation is continued for 30 minutes. The mixture is then cooled to about 54° C. and the remaining one-half of the 2-pyrrolidinone and the perfume are added and mixing is continued for an additional 10 minutes. The final mixture is then cooled to room temperature and is ready for use. The mixture is a thick creamy liquid oil-in-water emulsion.

This composition when applied to the skin produces a moisturization and flexibilization of the skin which is superior to that which is obtained with similar compositions wherein substantially all of the 2-pyrrolidinone is introduced into the composition by addition to the water phase before forming the emulsion or by addition to the total emulsion after it is formed.

In the foregoing example, a composition having substantially similar characteristics and skin conditioning effectiveness is obtained when the balance (i.e., the second 4%) of 2-pyrrolidinone is added to the water component before the water component is added to the oil component.

What is claimed is:

1. A skin conditioning composition in the form of an oil-in-water emulsion comprising:

A from about 1% to about 25% by weight of an oil component which is physiologically acceptable for placement on the skin, and in which 2-pyrrolidinone is freely miscible when said oil component is in the liquid state; said oil component being selected from the group consisting of lanolin fatty acids, isopropyl esters of lanolin fatty acids, hydroxylated lanolin, straight chain fatty acids containing from about 10 to about 20 carbon atoms, straight chain fatty alcohols containing about 10 to 20 carbon atoms and mixtures thereof;

B. from about 1% to about 20% by weight 2-pyrrolidinone;

C. from about 50% to about 95% by weight water; and

D. an amount of oil-miscible emulsifier sufficient to achieve an emulsion between components A, B and C; said composition being prepared by a process comprising the steps of 1. liquifying the oil component by bringing it to a temperature at which it is liquid;
   2. mixing the emulsifier and from about 10% to about 95% by weight of the total amount of 2-pyrrolidinone to be used in said composition into said oil component;

3. dissolving the balance of the 2-pyrrolidinone into the water; and
4. mixing the water solution of step (3) into the mixture of step (2) to form an emulsion.

2. The composition of claim 1 wherein the amount of 2-pyrrolidinone is from about 5% to about 15%, and from about 25% to about 75% of the total amount of said 2-pyrrolidinone is mixed into the oil component in Step (2).

3. The composition of claim 2 wherein the emulsifier is a nonionic surfactant.

4. The composition of claim 3 wherein the emulsifier is present at a level of from about 0.05% to about 10% of the composition and is selected from the group consisting of fatty acid monoglycerides wherein the fatty acid group contains from about 10 to about 20 carbon atoms, alkoxylated nonionic surfactants and mixtures thereof.

5. The composition of claim 4 wherein the oil component is present at a level of from about 5% to about 15% of said composition and is selected from the group consisting of lanolin fatty acids, isopropyl esters of lanolin fatty acids, hydroxylated lanolin, cetyl alcohol, stearyl alcohol, stearic acid and mixtures thereof and the emulsifier is a mixture of glycerol monostearate and polyoxypropylene (15) stearyl ether.

6. The compositon of claim 5 wherein after step (2) the water is mixed into the mixture of step (2) to form an emulsion and then the balance of the 2-pyrrolidinone is mixed into said emulsion.

* * * * *